United States Patent [19]

Ngai et al.

[11] Patent Number: 5,880,326
[45] Date of Patent: Mar. 9, 1999

[54] MODELS FOR MEASURING THE SENSE OF SMELL

[75] Inventors: John J. Ngai; Lisa J. Brunet, both of Berkeley, Calif.

[73] Assignee: The Regents of the University of California, Oakland, Calif.

[21] Appl. No.: 735,828

[22] Filed: Oct. 23, 1996

[51] Int. Cl.$^6$ .............................. C12N 5/00; C12N 15/00; A61K 49/00
[52] U.S. Cl. .................. 800/2; 800/DIG. 1; 435/172.3; 424/9.1
[58] Field of Search .................................. 800/2, DIG. 1; 435/172.3; 424/9.1

[56] References Cited

PUBLICATIONS

M Barinaga (1996) Science 274: 500–501.
H Komatsu et al (1996) Neuron 17: 707–718.
P Sengupta et al (1994) Cell 79: 971–980.
RL Davis et al (1995) Molecular and Cellular Biochemistry 149/150:271–278.
M Cobb (1996) Genetics 144: 1577–1587.

*Primary Examiner*—Bruce R. Campell
*Attorney, Agent, or Firm*—Richard Aron Osman

[57] ABSTRACT

The invention provides methods and compositions for measuring the sense of smell, including animals having general anosmia as a result of a genetic mutation. The genetic mutation disrupts a function of a protein required for cyclic nucleotide mediated signal transduction in olfactory neurons in the animal. The invention also encompasses methods of making and using such animals, such as methods of characterizing the effect of a stimulus on the subject mutant animals by contacting the animal with a stimulus and measuring a response of the animal to the stimulus, wherein the presence of a response indicates that the stimulus evokes a non-olfactory response.

9 Claims, 6 Drawing Sheets

Mineral oil

2-Hexyl-pyridine

Isomenthone

Citralva

Geraniol 0.2 s

MODELS FOR MEASURING THE SENSE OF SMELL

The research carried out in the subject application was supported in part by grants from the National Institutes of Health. The U.S. Government may have rights in any patent issuing on this application.

INTRODUCTION

1. Field of the Invention

The field of the invention is models for measuring an animal's sense of smell.

2. Background

The olfactory system is capable of recognizing and discriminating thousands of different odorant molecules. This complex process of sensory perception involves the activation of primary sensory neurons, the olfactory neurons, within the olfactory epithelium of the nose. Odorants elicit an inward (depolarizing) current across the plasma membrane of the sensory cilia of these cells, which lead to the generation of action potentials, and ultimately, the transmission of sensory information to the brain. The excitatory signaling in olfactory neurons is thought to be initiated by specific interactions between odorants and olfactory receptors, and perhaps additional accessory proteins which facilitate odorant-receptor binding.

The binding of an odorous ligand with its receptor is thought to be transduced into an excitatory signal in the olfactory neuron through distinct pathways. In vitro biochemical approaches have shown that some odorants elicit an increase in the intracellular second messenger cyclic AMP (cAMP), whereas other odorants cause an increase in the second messenger inositol trisphosphate ($IP_3$); i.e. cAMP mediates excitatory responses to one subset of odorants, while $IP_3$ mediates responses to another subset of odorants. Consistent with the proposed role of cAMP in olfactory signaling, a specific $G_{s\alpha}$-like G protein isoform, termed $G_{olf}$, as well as type III adenylyl cyclase are highly enriched in olfactory sensory cilia. Odorant-evoked elevations in cAMP are thought to directly activate a cation-selective cyclic nucleotide-gated (CNG) channel, resulting in membrane depolarization and the generation of action potentials. Similarly, and consistent with the proposed role of $IP_3$ in olfactory signaling, an $IP_3$ receptor and an $IP_3$-gated channel protein have been identified in olfactory cilia.

Relevant Literature cAMP mediated olfactory responses are reported in Pace et al., 1985; Sklar et al., 1986; and Breer et al., 1990. $IP_3$ mediated olfactory responses are reported in Huque and Bruch, 1986; Boekhoff et al., 1990 and Breer and Boekhoff, 1991. Other components of the olfactory signal response pathway include G proteins, (e.g. Jones and Reed, 1989; and Bakalyar and Reed, 1990), a CNG channel (e.g. Nakamura and Gold, 1987; Kurahashi, 1989; Kurahashi, 1990; Firestein et al., 1991; Frings and Lindemann, 1991; Lowe and Gold, 1993a).

SUMMARY OF THE INVENTION

The invention provides methods and compositions relating to models for olfactory responses, including animals having general anosmia as a result of a genetic mutation. In preferred embodiments, the genetic mutation disrupts a function of a protein required for cyclic nucleotide mediated signal transduction in olfactory neurons in the animal, preferably an ion channel. The invention also encompasses methods of making and using such animals. For example, the invention includes methods of characterizing the effect of a stimulus on the subject mutant animals by contacting the animal with a stimulus and measuring a response of the animal to the stimulus, wherein the presence of a response indicates that the stimulus evokes a non-olfactory response in the animal.

DETAILED DESCRIPTION OF PREFERRED EMBODIMENTS OF THE INVENTION

Figure 1:
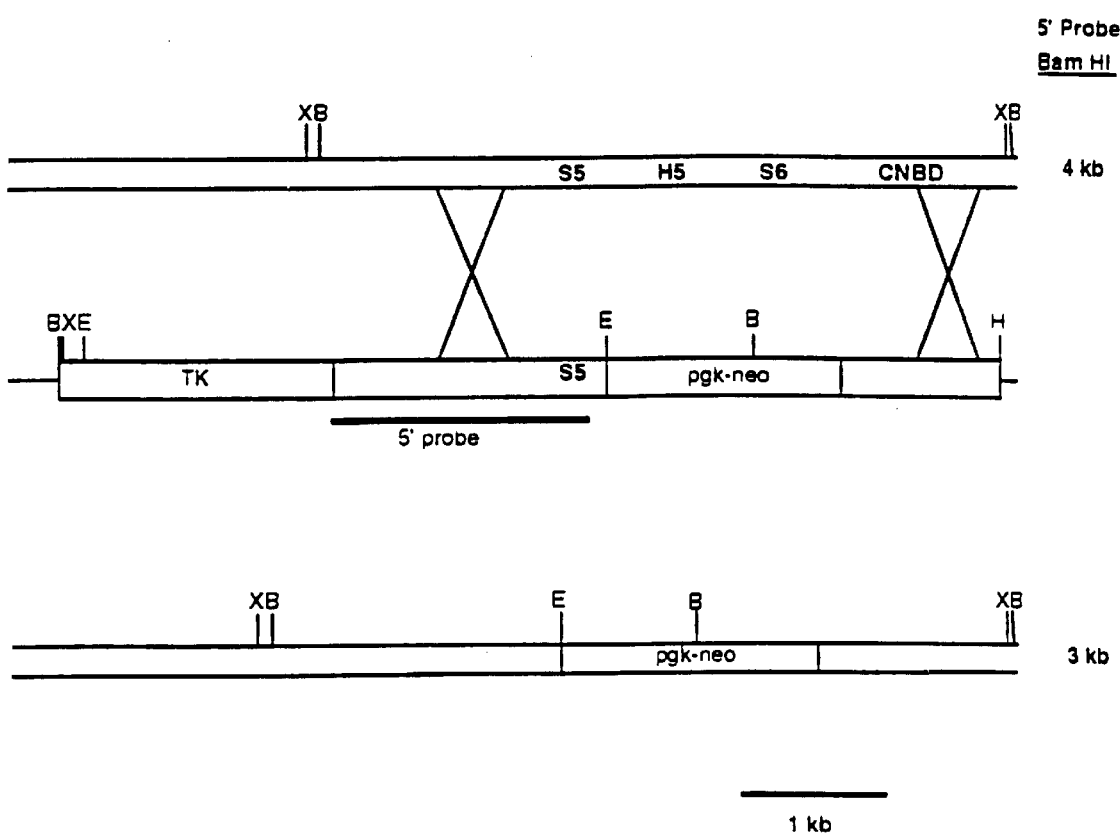
FIG. 1. Targeted Disruption in the Olfactory CNG Channel Alpha Subunit Gene Homologous recombination of the wild type olfactory CNG channel gene (top line) with the targeting vector (middle line) results in a disrupted CNG channel gene (bottom line).

The invention provides methods and compositions relating to models for measuring an animal's sense of smell including animals having general, and preferably comprehensive, anosmia as a result of a genetic mutation. General anosmia refers to an impaired sense of smell across numerous different classes of odorants, including both odorants reported to act via a cAMP-mediated pathway and odorants reported to act via an $IP_3$ pathway. Comprehensive anosmia refers to an impaired sense of smell of essentially all volatile odorants. The impairment with a given odorant is at least 90%, preferably at least 96%, more preferably at least 99%, and most preferably absolute, i.e. undetectable against background responsiveness.

Anosmia may be evaluated by any convenient means, depending on the animal, odorant, throughput requirements, etc. Suitable assays include a variety of attraction or aversion based behavioral assays, electrophysiology based assays, binding assays, etc. Such olfactory assays are well known in the art; exemplary assays disclosed or cited herein. Preferred animals are vertebrates, especially mammals.

In preferred embodiments, the genetic mutation disrupts a function of one or more proteins required for cyclic nucleotide mediated signal transduction in olfactory neurons in the animal, preferably including a G protein, a kinase, a phosphodiesterase, a cyclase, an olfactory receptor, an odorant binding protein, a transcription factor or an ion channel, more preferably, the animal's olfactory CNG channel. The requisite mutation disrupts cyclic nucleotide mediated signaling sufficient to effect the requisite anosmia, and may comprise disruptions in multiple genes encoding different proteins, but is preferably confined to a single gene. The disrupted gene function(s) may operate at any stage of signal transduction, including odorant binding, transmembrane signal transduction, regulation of signal transduction components including regulators of transcription, translation and localization, etc. The mutation may take a variety of forms including insertion(s), deletion(s), substitution(s), etc., so long as gene product function is disrupted and the requisite anosmic phenotype is obtained. A wide variety of methods may be used for making animals having the requisite mutation, including gene targeting and transgenic technologies, random or directed mutagenesis and selection, etc. Such mutagenesis methods are well-known in the art; exemplary methods are disclosed and/or cited herein.

The subject animals find a wide variety of commercial applications. For example, the invention includes methods of characterizing the effect of a stimulus on the subject mutant animals, and/or distinguishing olfactory responses from non-olfactory responses, by contacting the animal with a stimulus and measuring a response of the animal to the stimulus, wherein the presence of a response indicates that the stimulus evokes a non-olfactory response in the animal. A wide variety of stimuli/response patterns may be evaluated including responses associated with therapeutic or prophylactic pharmaceutical administration, exposure to food or nutrients, pheromones, light, etc. Such assays are used, for example, to distinguish main from accessory olfactory responses mediated through the vomeronasal organ (see, Berghard et al. PNAS 93, 2356–2359, 1996; Berghard and Buck, J Neurosci. 16, 909–918, 1996; and Halpern M. Ann Rev Neurosci. 10, 325–362, 1987).

The following experimental section/examples are offered by way of illustration and not by way of limitation.

EXAMPLES

1. Disruption of the Mouse Olfactory CNG Channel by Homologous Recombination

CNG channels are heterotetramers (Liu et al., 1996) composed of ion-conducting alpha subunits (Kaupp et al., 1989; Dhallan et al., 1990; Goulding et al., 1992) and modulatory beta subunits (Chen et al., 1993; Bradley et al., 1994; Liman and Buck, 1994; Korschen et al., 1995). We therefore chose to mutate the olfactory CNG channel alpha subunit gene in order to ablate channel function. We designed a targeting vector which, upon homologous recombination within the olfactory CNG channel alpha subunit gene, would delete a portion of the channel that includes the extracellular loop following the fifth membrane spanning region (S5), the putative pore-forming region (H5), the sixth membrane spanning region (S6), and a portion of the intracellular carboxy-terminal tail (FIG. 1; see also Goulding et al., 1992). Thus, any protein product derived from this disrupted gene would not be expected to form a functional channel subunit.

Embryonic stem (ES) cells derived from the 129/Sv strain of inbred mice were transfected with the targeting construct, and clones were isolated and screened for homologous recombination by Southern blot analysis (see Experimental Procedures). The resultant hybridization pattern indicates that the olfactory CNG channel gene underwent homologous recombination with the targeting vector in one of these cell lines. Interestingly, no wild type band is observed with the CNG channel probe in the homologous recombinant. Since the ES cell line we used has a normal XY karyotype (Szabo and Mann, 1994), this suggests that the olfactory CNG channel gene is located on the X chromosome.

ES cell lines containing the mutant olfactory CNG channel gene were expanded and used to generate chimeric mice. A total of seven chimeric mice were obtained using two independent cell lines. One male chimera transmitted the mutation through the germline when crossed with wild type females, as judged by detection of the neomycin resistance gene in F1 offspring by PCR analysis. An initial analysis of 37 F1 pups indicated that 17 out of 18 female offspring contained this gene, whereas all 19 males were negative. The strict segregation of the targeted gene to female F1 offspring confirms that the olfactory CNG channel alpha subunit gene resides on the X chromosome.

2. Early Postnatal Lethality in Mice Hemizygous for the CNG Channel Mutation

Upon crossing F1 heterozygous mutant females with wild type males, we found that an unusual number of F2 pups died within one to two days after birth. While these pups appeared healthy and pink immediately after birth, their stomachs remained devoid of milk and they quickly became dehydrated. These animals appeared unable to locate the mother's nipple and suckle, even when placed directly next to a nipple in the absence of any competing littermates. The dead pups were invariably males; genotypic analysis confirmed that they were also hemizygous for the targeted CNG channel gene. Since olfactory cues are thought to play an important role in suckling behaviors (Teicher and Blass, 1977; Hudson and Distel, 1986; Risser and Slotnick, 1987), these observations gave an early hint that olfactory signaling was profoundly affected in the hemizygous mutant animals. Interestingly, a small percentage of mutant males (ca. 1–10%) learned to suckle effectively (presumably based on non-olfactory cues) and survived to adulthood. Owing to the difficulty in obtaining adult animals homozygous for the channel mutation, the studies described below were performed on one day-old pups.

3. Expression of Olfactory Neuron Markers is Normal in Hemizygous Mutants

The goal of this study is to define the role of the CNG channel in olfactory signaling by studying the physiological effects of a targeted mutation in the olfactory CNG channel alpha subunit gene. This requires that we first establish that any effects of this mutation on signal transduction are due to an absence of functional CNG channels in mature olfactory neurons, rather than a non-specific effect on olfactory neuron maturation or structure. We therefore performed RNA in situ hybridizations on olfactory epithelium preparations using molecular markers for mature olfactory neurons.

One such marker is the olfactory marker protein (OMP), an abundant cytoplasmic protein of unknown function which is expressed only in mature olfactory neurons (Margolis, 1985). In situ hybridizations with an OMP probe demonstrate the expression of OMP RNA in olfactory neurons throughout the sensory epithelium of the medial septum and complex nasal turbinates of both wild type and mutant animal. The density of olfactory neurons in mutants is indistinguishable from that in wild type epithelium, as judged by the level of OMP expression. In situ hybridizations using a probe complementary to the disrupted portion of the CNG channel gene confirm that intact CNG channel alpha subunit transcripts are not expressed in olfactory neurons of mutant animals.

We next examined the expression patterns of odorant receptor genes in the olfactory epithelium. Odorant receptors are expressed in 3 to 4 distinct zones of the olfactory epithelium; each zone comprises a hemicylindrical ring along the anterior-posterior axis (Strotmann et al., 1992; Ressler et al., 1993; Vassar et al., 1993). Thus, in coronal sections, the expression zones appear as concentric dorsomedial to ventrolateral arcs. We find that odorant receptor expression is indistinguishable in mutant and wild type pups. For example, in both wild types and mutants, odorant receptor M50 is expressed appropriately in the ventrolateral-most zone, whereas odorant receptor K4 is expressed in a medial zone. From a survey of numerous tissue sections, the frequency of olfactory neurons expressing each of these receptors is similar in both cases. Thus, odorant receptor expression appears unaffected by the targeted CNG channel mutation.

4. Olfactory Signal Transduction Components Are Expressed in Appropriate Subcellular Structures in Hemizygous Mutants The cilia of olfactory neurons are specialized structures whose function is to receive odorant stimuli and transduce odorant-receptor binding into changes in intracellular second messengers and membrane potential (Pace et al., 1985; Lowe and Gold, 1991; Kurahashi and Kaneko, 1993; Kleene et al., 1994). It is therefore important to show that olfactory cilia are intact in CNG channel mutants and that key signal transduction molecules are appropriately expressed in these structures. Toward this end, we performed immunohistochemistry on olfactory epithelium from wild type and mutant animals, using an antibody directed against type III adenylyl cyclase and an antibody directed against a common epitope found in $G_{s\alpha}$ and $G_{olf}$. Both Golf and type III adenylyl cyclase are highly enriched in olfactory cilia (Jones and Reed, 1989; Bakalyar and Reed, 1990). We find that type III adenylyl cyclase is localized to the olfactory cilia in mutant olfactory epithelium in a pattern indistinguishable from that found in wild type animals. Similarly, the anti-Gsa/$G_{olf}$ antibody shows strong immunoreactivity to the olfactory cilia in both wild type and mutant preparations. Thus, in mice hemizygous for the CNG channel mutation, expression of odorant receptors, G protein, and adenylyl cyclase is normal in olfactory neurons and the olfactory cilia appear intact.

Previous studies have shown that $G_{olf}$ is localized in olfactory neuron axons in addition to the sensory cilia. Immunohistochemistry with the anti-Gsa/$G_{olf}$ antibody shows the expected localization of signal to the subepithelial axon fascicles in wild type and mutant animals. The population of olfactory neuron axons in mutants also appears to innervate the glomerular layer of the olfactory bulb. These observations indicate that olfactory neuron structure is normal in mice hemizygous for the targeted CNG channel mutation.

Figure 2A:
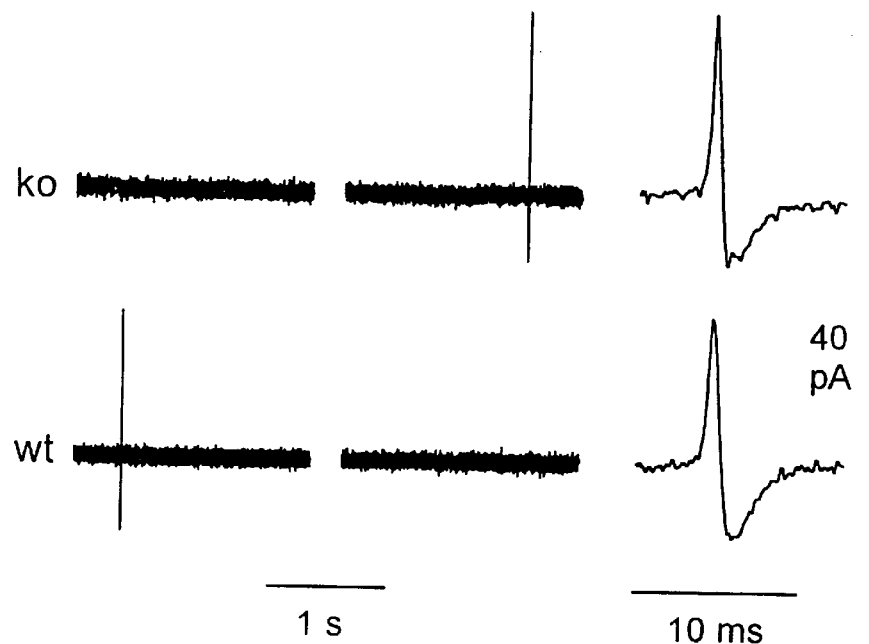
FIGS. 2A and 2B. Single Cell Recordings Demonstrate that Olfactory Neuron Membrane Properties are Normal in CNG Channel Hemizygous Mutants. (A) Representative traces from patch clamp recordings (ko, hemizygous mutant; wt, wild type). (B) Mean spike rates were compared between wild type and mutant olfactory neurons (n=3 cells from 3 wild type animals; n=4 cells from 3 mutant animals). Mean values are represented by solid bars, with the respective 95% confidence intervals indicated by error bars. Spike rates are low in cells from both backgrounds, and the difference between the means is not statistically significant (p=0.25).
Figure 2B:
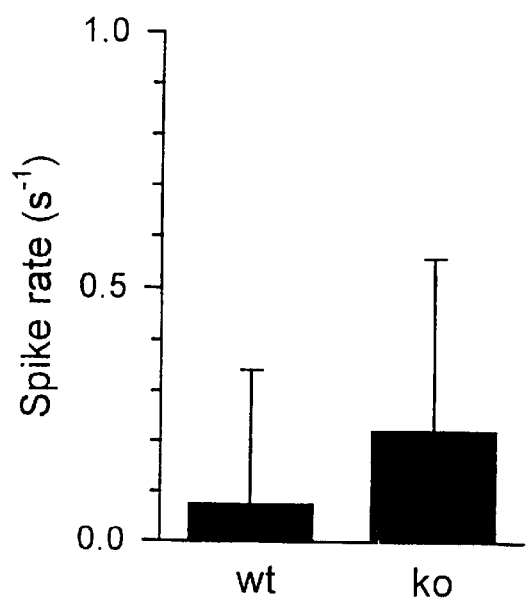
Figure 3A:
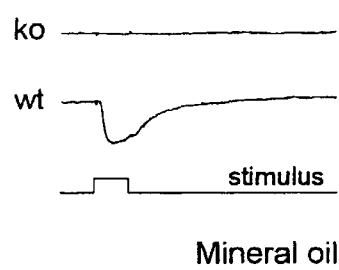
FIG. 3. EOG Recordings from Olfactory Epithelium of Wild Type and Hemizygous Mutant Pups.
Figure 3B:
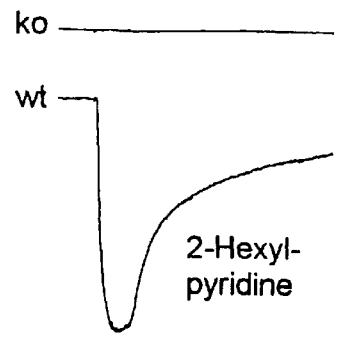
Figure 3C:
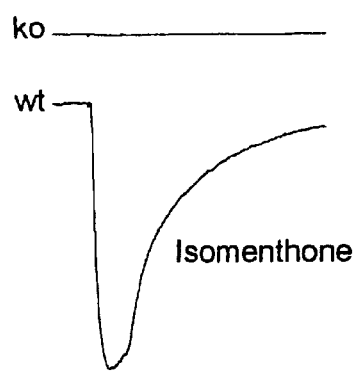
Figure 3D:
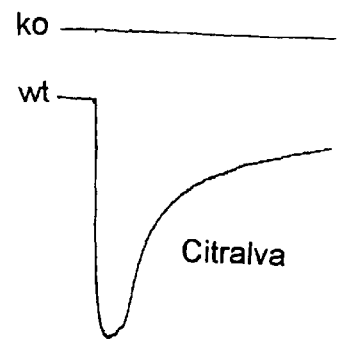
Figure 3E:
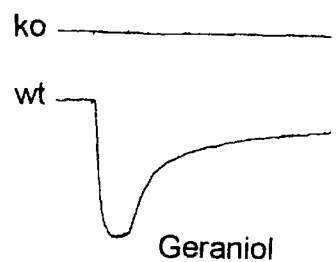
Figure 3F:
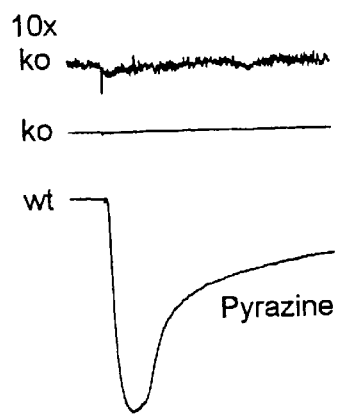
Figure 3G:
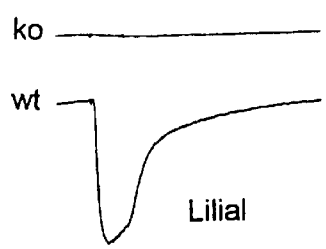
Figure 3H:
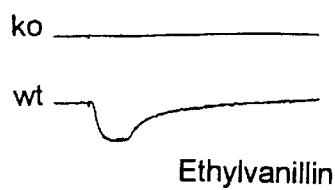
Figure 3I:
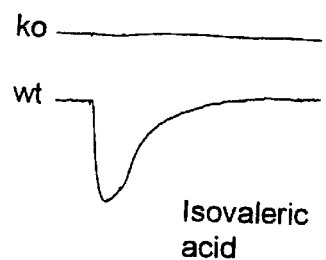
Figure 3J:
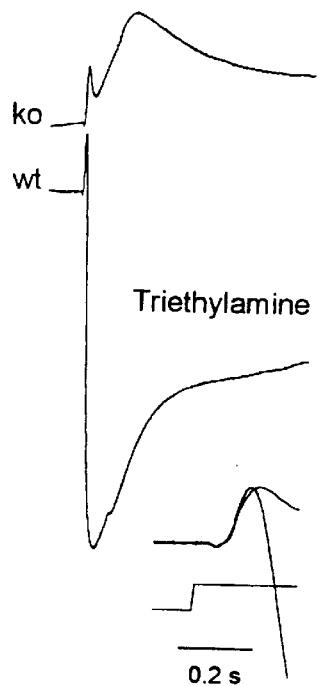
Figure 3K:
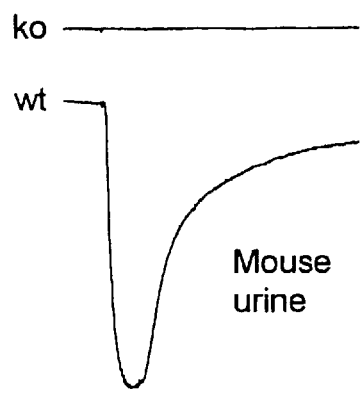
Figure 3L:
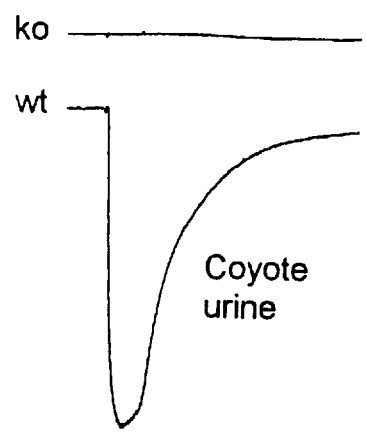
Figure 3M:
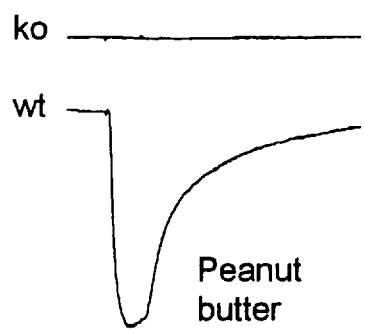

5. Electrophysiological Properties are Normal in Olfactory Neurons from Hemizygous Mutants We wish to determine whether excitatory olfactory signaling is altered by the genetic removal of the olfactory CNG channel. It is therefore important to establish that any differences in odorant-evoked responses between wild type and mutant mice are caused by the absence of the signal transducing CNG channel, and not by abnormal electrophysiological properties of the mutant neurons. For example, if mutant neurons have an abnormally positive resting potential, this would decrease odorant responses mediated by all excitatory pathways. A normal resting potential in mutant mice can be inferred if the rate of spontaneous action potential generation is similar to the rate observed in wild type mice. Since the threshold for spike generation lies close to the resting membrane potential Lynch and Barry, 1989), a difference in resting potential between mutant and wild type olfactory neurons would be manifested as a difference in the rate of spontaneous spike generation. We find that spontaneous action potentials occur at similarly low rates in cells from wild type and mutant pups (FIGS. 2A, 2B). The pattern of spontaneous action potential generation in mutant cells therefore indicates that the resting potential of olfactory neurons is also similar to that of wild type cells. Moreover, the time course of individual action potentials is the same in cells from both backgrounds (FIGS. 2A, 2B), further indicating that the voltage-dependent properties of the mutant olfactory neuron membrane are normal. Thus, any observed differences in olfactory signaling between mutant and wild type preparations (described below) can be ascribed to an absence of functional CNG channels rather than an alteration of resting membrane properties.

6. Absence of Odorant-Evoked Signaling in Olfactory Neurons of Hemizygous Mutant Animals Having established that the expression of olfactory neuron-specific markers and the resting membrane properties of olfactory neurons are unaffected in mice hemizygous for the targeted CNG channel mutation, we next turned to an analysis of odorant-stimulated olfactory neuron function. Since the CNG channel alpha subunit is required for CNG channel function (Kaupp et al., 1989; Dhallan et al., 1990; Goulding et al., 1992; Chen et al., 1993; Liman and Buck, 1994), mice hemizygous for a mutation in this gene provide a means to assess the role of this channel in olfactory signaling.

To assess olfactory neuron function, we recorded odorant-evoked changes in the voltage across the olfactory epithelium. This measurement, termed the electro-olfactogram (EOG; Ottoson, 1956), is an extracellular field potential that locally summates the activity of cells in the olfactory epithelium and thus provides a sensitive and facile assay for neuronal function. For most odorants, the EOG consists of a transient negative potential generated by the extracellular current flow resulting from an inward current across the olfactory cilia and an equivalent outward current across the dendritic and somatic membranes (Lowe and Gold, 1991). Some odorants evoke an initial positive transient, followed by the more common negative response. The positive component, but not the negative component of the EOG persists in epithelia whose receptor cells have been destroyed by denervation and is correlated with mucus secretion by non-neuronal supporting cells (Okano and Takagi, 1974). Thus, the positive component arises independently of the signal transduction mechanism within olfactory neurons.

EOG recordings were performed on olfactory epithelium preparations from 1 day-old pups using the following compounds as stimulants: 2-hexylpyridine, isomenthone, citralva, and geraniol, which have been reported to elicit increases in cAMP (Sklar et al., 1986; Breer and Boekhoff, 1991); and pyrazine, lilial, ethylvanillin, isovaleric acid and triethylamine, which have been reported to elicit increases in IP$_3$ (Boekhoff et al., 1990; Breer and Boekhoff, 1991). The concentrations of individual odorant stimuli were chosen to produce as large a response as possible in control preparations without causing an excessively long recovery time (see Experimental Procedures). To assess olfactory function in response to more complex or "natural" stimuli, EOG recordings were also carried out using 3 chemically undefined odorous substances: C57BL/6 mouse urine, coyote urine, and peanut butter. The urine samples were included in this analysis owing to their efficacies in eliciting olfactory-mediated behaviors. Mice can discriminate other mice of different genetic backgrounds based on odorants present in urine (Yamaguchi et al., 1981), and coyote urine contains aversive odorant cues which signal the presence of a predator (Nolte et al., 1994). Peanut butter was tested because of its potency as an attractive food source for mice (e.g., as bait in mouse traps; Davis, 1956).

FIG. 3 shows representative EOG recordings from a wild type female and a hemizygous mutant male. EOG recordings were typically performed by placing the electrode in the approximate middle of the first (anterior-most) turbinate, since responses to odorants in control preparations were largest at this location. For each odorant, the hemizygous mutant response (ko) is plotted directly above the wild type (wt) response. A slow negative response is observed following exposure of the wild type olfactory epithelium to each test odorant. Responses to odorants reported to elicit increases in cAMP are included in the top row of the figure, whereas responses to odorants reported to elicit increases in $IP_3$ are shown in the middle row. These response waveforms are typical of those observed in mice (e.g., see Wang et al., 1993). A small response is observed with mineral oil (the solvent carrier for all odorants except isovaleric acid and ethylvanillin, which were diluted in water), and is probably due to odorous hydrocarbons present in the mineral oil used for these experiments. By striking contrast to the responses found in wild type epithelium, no detectable negative EOG is observed in the hemizygous mutant epithelium with any of the odorants tested. The absence of a detectable response is seen more clearly in the pyrazine knockout trace plotted at ten times higher gain (10×ko).

Considering that sensitivity to specific odorants varies across the surface of the olfactory epithelium (Thommesen and Doving, 1977; Ezeh et al., 1995), presumably due to the spatially restricted expression of individual olfactory receptor proteins to distinct longitudinal zones (Strotmann et al., 1992; Ressler et al., 1993; Vassar et al., 1993), it is formally possible that responses to some odorants might be detectable in knockout mice at other recording locations. To investigate this possibility, we carried out EOG recordings at two other locations in addition to the middle of the first turbinate: near the superior edge of the first turbinate and near the middle of the third turbinate. Activity from cells was therefore sampled across multiple odorant receptor expression zones. Identical results showing a complete absence of negative EOG responses were obtained at each of the three recording locations in 6 hemizygous mutant pups.

The only response remaining in the mutant mouse was a rapidly rising positive potential upon stimulation with triethylamine, and is most obvious in the mutant owing to the absence of the negative EOG response. In normal olfactory epithelium, the summation of positive and negative components with slightly different latencies results in an intial positive transient followed by the more prolonged negative response (see inset below the triethylamine panel in FIG. 3, which superimposes the wild type and hemizygous mutant responses on an expanded time scale). The positive EOG reflects an odorant-evoked secretory mechanism in non-neuronal supporting cells (Okano and Takagi, 1974); its persistence in hemizygous mutant mice therefore is expected. Since the expression of the olfactory CNG channel is restricted to olfactory neurons (Dhallan et al., 1990; Goulding et al., 1992), the absence of the negative EOG in knockout mice also confirms that the negative EOG indeed is of neuronal origin.

Figure 4:
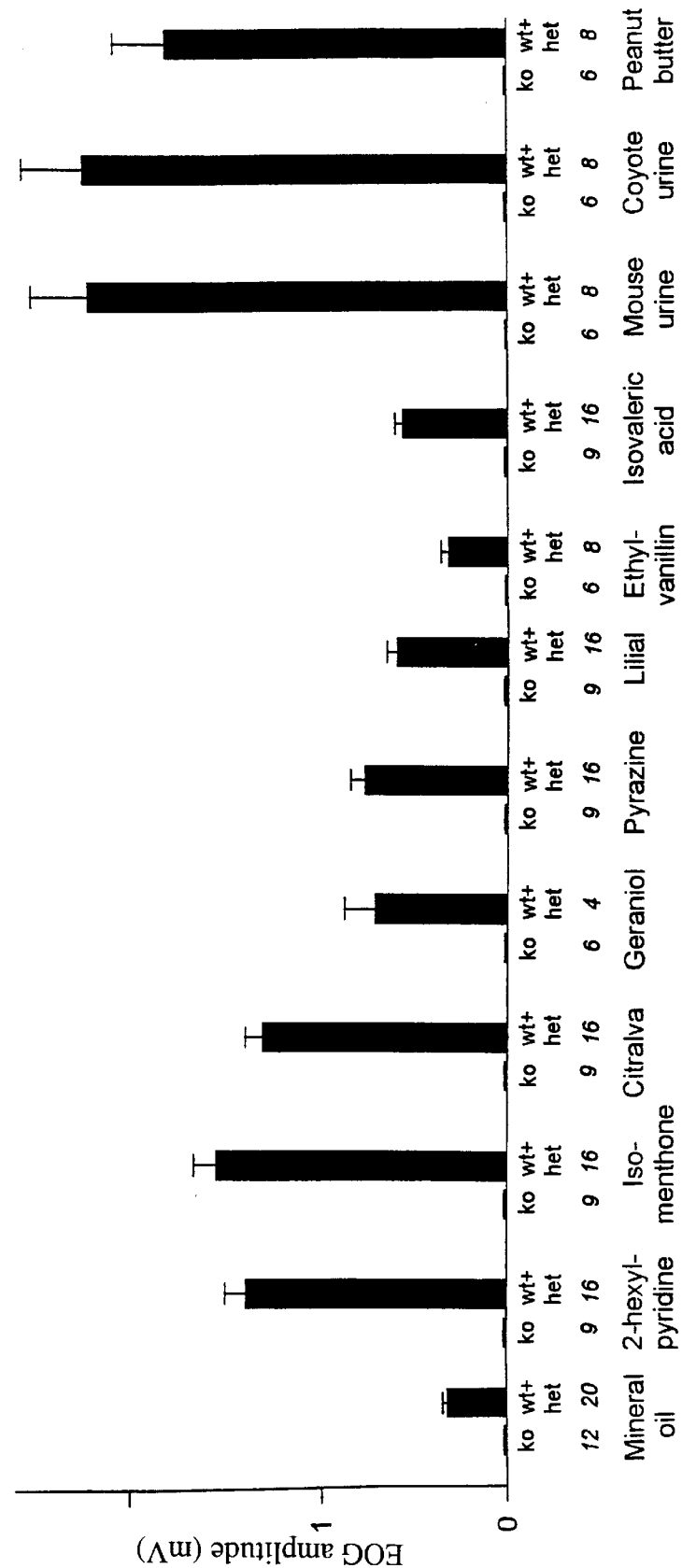
FIG. 4. Quantitation of Negative EOG Response Amplitudes.

We quantitated EOG response amplitudes from 6 litters of inbred F2 pups derived from crosses between 129/Sv F1 heterozygous females (+/−) and 129/Sv wild type males (+/o) (FIG. 4). The negative EOG was always detected in wild type and heterozygous mice (20 pups) but was never detected in mice bearing the (−/o) genotype (12 pups). Although a negative EOG was not observed in hemizygous mutant mice, we cannot rule out a response smaller than the noise of our recordings. Thus, in FIG. 4, the values for hemizygous mutant responses are each expressed as an upper limit estimated as twice the magnitude of the peak-to-peak noise of the recording (peak-to-peak noise was typically <0.01 mV). For all odorants tested, mean EOG responses of wild type and heterozygous mutant pups were highly significantly different from those of hemizygous mutant males (see Experimental Procedures). One might predict that heterozygous female mutants would exhibit EOG responses that are ~50% smaller than those found in wild type animals due to random X-inactivation. Response amplitudes from heterozygous mutant females were not significantly different than those from wild type preparations, however (e.g., p=0.28 for pyrazine responses). Our inability to discern this difference may be due to the steps we employed to minimize recording noise; these methods introduced some variability in the EOG recordings, possibly obscuring any small quantitative differences (see Experimental Procedures).

To rule out the possibility that the severity of the knockout phenotype is influenced by genetic background or due to a second, unlinked mutation, we performed EOG recordings on F2 and F3 generation mice derived from successive back-crosses onto the FVB inbred background (see Experimental Procedures). Fourteen F2 generation mice (from a total of 72) displayed aberrant EOG responses typical of hemizygous mutants; all 14 of these animals were subsequently determined to have the (−/o) genotype. Similarly, analysis of 25 F3 offspring revealed 4 pups which failed to show a negative EOG response to any of the odorants tested; all 4 were hemizygous (−/o) mutant males. In summary, irrespective of genetic background, all 30 pups with the (−/o) genotype failed to exhibit a negative EOG, whereas each of the 98 wild type or heterozygous mice always showed prominent odorant-evoked negative EOG responses. Taken together, our results demonstrate that the olfactory CNG channel is required for excitatory signaling in response to all of the odorants tested, including those which have been reported to elicit elevations in $IP_3$, but not cAMP (Boekhoff et al., 1990; Breer, Boekhoff, 1991).

7. Experimental Procedures a) Derivation of Mice Harboring a Targeted Disruption in the Gene Encoding the Alpha Subunit of the Olfactory CNG Channel A sequence encoding a portion of the mouse olfactory CNG channel alpha subunit gene was isolated by reverse transcriptase-PCR, using mouse olfactory epithelium RNA as a template. The PCR product, which corresponds to amino acids 289–560 of the rat olfactory CNG channel protein (Dhallan et al., 1990), was subcloned into pBluescript and subjected to DNA sequencing to confirm its identity. Genomic clones containing the mouse olfactory CNG channel alpha subunit gene were isolated from a mouse 129/Sv genomic library using the mouse CNG channel PCR clone as a probe. DNA fragments from the olfactory CNG channel alpha subunit gene were then used to construct a targeting vector in which the neomycin gene (driven by the PGK promoter) is flanked by ~2 kb of genomic DNA as well as the herpes virus thymidine kinase gene on one side and ~1 kb of genomic DNA on the other side (see FIG. 1). Homologous recombination of the targeting vector with the olfactory CNG channel gene results in the replacement of channel coding sequence corresponding to amino acids 304–470 of the rat olfactory CNG channel (Dhallan et al., 1990) with the PGK-neomycin resistance gene.

Embryonic stem (ES) cells derived from the 129/Sv strain of inbred mice (a gift from Dr. Colin Stewart) were transfected with the targeting construct by electroporation and placed under double selection with G418 and FIAU (Ramirez-Solis et al., 1993). Clones were isolated and screened for homologous recombination by Southern blot analysis. Embryonic stem cell lines containing the mutant olfactory CNG channel gene were expanded and used to generate chimeric mice by aggregation with morulae derived from outbred CD1 mice (Stewart, 1993). A total of seven chimeric mice were obtained from aggregations using two independent cell lines.

Chimeras were mated with either 129/Sv or FVB female mice to produce F1 offspring. Genotyping of offspring was performed by Southern blotting as well as by PCR for the neomycin resistance gene on genomic DNA from F1 offspring. Pups were sexed by PCR using primers for the Y chromosome-specific SRY gene (Gubbay et al., 1992).

One male chimera transmitted the mutation through the germline when crossed with wild type females. To obtain F2 generation mice on the inbred 129/Sv background, heterozygous female F1 mice derived from crosses between the original chimera and 129/Sv females were mated with wild type 129/Sv males. To obtain F2 generation mice on the FVB background, heterozygous F1 females derived from crosses between the chimera and FVB females were mated with wild type FVB males. Females resulting from these latter crosses were then mated with wild type FVB males to produce F3 generation mice on the FVB background.

b) In Situ Hybridization and Immunohistochemistry

Coronal sections were prepared from the snouts of 1 day-old F2 male pups which were derived on the FVB background. Localization of OMP and olfactory CNG channel alpha subunit RNAs was performed on 20 -thick fresh frozen sections using digoxigenin-labeled RNA probes (Schaeren-Wiemers and Gerfin-Moser, 1993). For OMP, a rat cDNA was used as a template for probe synthesis (Dancinger et al., 1989); for the olfactory CNG channel, a probe was synthesized from a mouse sequence corresponding to amino acids 289–560 of the rat olfactory CNG channel coding region. Odorant receptor RNAs were localized within 20 -thick fresh frozen sections using 33P-labeled antisense RNA probes for mouse odorant receptors M50 and K4 (Ressler et al., 1993), essentially as described (Wilkinson et al., 1987).

Immunohistochemistry was performed on 10 -thick frozen sections prepared from snouts which were fixed in 4% paraformaldehyde and cryopreserved in 30% sucrose prior to embedding. Tissue sections were reacted with rabbit polyclonal anti-peptide antibodies specific for Type III adenylyl cyclase or $G_{s\alpha}/G_{olf}$ (Santa Cruz Biotechnology, Inc.) according to conditions recommended by the manufacturer. Specifically-bound primary antibody was localized with a horseradish peroxidase-conjugated anti-rabbit IgG, followed by a chromogenic reaction using diaminobenzidine/$H_2O_2$ as a substrate.

c) Electrophysiology

One day-old mouse pups were sacrificed by decapitation; each head was bisected through the septum with a razor blade to expose the medial surfaces of the olfactory turbinates; the right or left sides were chosen at random for electrophysiological recording. The remainder of each animal was frozen and later genotyped and sexed by PCR analysis, using primers for the neomycin resistance gene and the male-specific SRY gene; these analyses were performed blind with regard to phenotype. Odorant stimulation and EOG recording were carried out as described (Wang et al., 1993). Switching between humidified clean and odorized air streams was accomplished by a pneumatically actuated 4-way slider valve. Odorized air was produced by blowing clean air through a horizontal glass cylinder that was half filled with the odorant solution. Peanut butter (Skippy "Creamy") was spread on a piece of filter paper that covered most of the inside surface of the glass tube. Odorant concentrations are expressed as the concentration of odorant in the liquid phase contained within the evaporation tubes, and were chosen to produce as large a response as possible in wild type mice without causing an excessively long recovery time. Each odorant was presented only once to a preparation with a 1 minute interval between different stimuli. No difference in response amplitudes was observed if the interval was increased to 2 minutes. The mineral oil used as a diluent for water-insoluble odorats was deodorized by passing through two 50 cm long silica gel columns. This reduced the amplitude of the response to mineral oil by about 8-fold.

Recording stability was improved by placing a drop of saline on the epithelial surface prior to recording and any excess was removed by aspiration. This procedure was repeated during the recording session if the baseline became unstable. Applying saline to the mucus layer probably introduced some variability in the thickness of the mucus layer, which may have also increased the variability of the EOG amplitude. The recorded signals were low pass filtered at 30 Hz and digitized at 125 Hz.

Cell-attached patch clamp recordings (Hamill et al., 1981) were performed on individual olfactory neurons in tissue slices, using solutions as described (Lowe and Gold, 1993b). Recordings were low pass filtered at 2 kHz and digitized at 8 Khz.

For the data depicted in FIG. 3, the following odorants were diluted in mineral oil (fold-dilutions from pure liquid stocks are indicated in parentheses): 2-hexylpyridine (10-3), isomenthone (10-3), citralva (10-3), geraniol(10-3), lilial (10-2), triethylamine (10-3) Pyrazine (a solid) was dissolved to a final concentration of 10-2M in mineral oil. Isovaleric acid (final concentration: 0.02M) and ethylvanillin (final concentration: 0.2M) were each diluted in water. Urine from C57BL/6 male mice, coyote urine (from meat-fed animals), and peanut butter were not diluted. In all cases, odorants were applied 1 second after the beginning of each trace for a duration of 1 second. The stimulus trace beneath the mineral oil response shows an example of the time course of the computer-controlled stimulus pulse. The small initial negative deflection in each EOG trace (most easily visible in each of the knockout traces) is a mechanical artifact caused by actuation of the valve used to switch air streams; a similar positive artifact occurs when the stimulus is switched back to clean air. The knockout trace in response to pyrazine is also shown at 10-fold higher gain (10×ko) to demonstrate the absence of a detectable negative EOG. The positive EOG of the mutant in response to triehylamine is of non-neuronal origin (Okano and Takagi, 1974; see the text), and superimposes with the initial transient positive response of the wild type trace (see inset with expanded time scale).

For the data depticed in FIG. 4, mean amplitudes of negative EOG responses were compared between hemizygous mutant mice (ko) and wild type plus heterozygous mice (wt+het) derived on the inbred 129/Sv background. Each mean value is represented by a solid bar, with the standard error of the mean indicated by an error bar. Mineral oil response amplitudes were subtracted from responses in which odorants were diluted in mineral oil. No detectable negative EOG was observed in hemizygous mutant pups. The data for these animals are therefore expressed as an upper limit based on twice the mean peak-to-peak noise of the respective recordings (range: 0.012 to 0.018 mV). Since no significant difference in response magnitudes was observed between wild type and heterozygous mutants, these animals were considered as a single group. In all cases, the differences between hemizygous mutant responses and wild type/heterozygote responses are statistically significant (p<0.0001 for all odorants except geraniol, for which p=0.0008). Sample sizes used to determine each value are indicated; a total of 32 mice were assayed.

8. Cited References

Anholt, R. R., and Rivers, A. M. (1990)Biochemistry 29,4049–4054. Bakalyar, H. A., and Reed, R. R. (1990) Science 250, 1403–1406. Boekhoff, I., Tareilus, E., Strotmann, J., and Breer, H. (1990) EMBO J. 9, 2453–2458. Borisy, F. F., et al.. (1992) Neurosci. 12, 915–923. Bradley, J., et al. (1994). Proc. Natl. Acad. Sci. USA 91, 8890–8894. Breer, H., and Boekhoff, I. (1991).Chem. Senses 16, 19–29. Breer, H., Boekhoff, I., and Tareilus, E. (1990). Nature 345, 65–68. Buck, L., and Axel, R. (1991). Cell 65, 175–187. Chen, T.-Y., et al. (1993). Nature 362, 764–767. Chen, T. Y., and Yau, K. W. (1994). Nature 368, 545–548. Cunningham, A. M., et al. (1993). Neuroscience 57, 339–352. Dancinger, E., et al. (1989). Proc. Natl. Acad. Sci. USA 86, 8565–8569. Davis, D. E. (1956) Manual for Analysis of Rodent Populations, Baltimore, Johns Hopkins Univ. Dhallan, R. S., Yau, K.-W., Schrader, K. A., and Reed, R. R. (1990). Nature 347, 184–187. Ezeh, P. I., Davis, L. M., and Scott, J. W. (1995). J. Neurophys. 73, 2207–2220. Firestein, S., Darrow, B., and Shepherd, G. M. (1991). Neuron 6, 825–835. Firestein, S., and Werblin, F. (1989). Science 244, 79–82. Frings, S. (1993). J. Gen. Physiol. 101, 1–24. Frings, S., and Lindemann, B. (1990). Biophys. J. 57, 1091–1094. Frings, S., and Lindemann, B. (1991). J. Gen. Physiol. 97, 1–16. Frings, S., Seifert, R., Godde, M., and Kaupp, U. B. (1995). Neuron 15, 169–179. Gordon, S. E., et al. (1995) Biophys. J. 69, 409–417. Goulding, E. H., et al.. (1992) Neuron 8, 45–58. Gubbay, J., et al. (1992).Proc. Natl. Acad. Sci. USA 89, 7953–7957. Hamill, O. P., et al. (1981). Pflugers Archiv. Eur. J. Physiol. 391,85–100. Hudson, R., and Distel, H. (1986). Physiol. Behav. 37, 123–128. Huque, T., and Bruch, R. C. (1986). Biochem. Biophys. Res. Comm. 137, 36–42. Jones, D. T., and Reed, R. R. (1989). Science 244, 790–795. Kalinoski, D. L., et al. (1992). Biochem. J. 281, 449–456. Kaupp, U. B., et al. (1989). Nature 342, 762–766. Kieene, S. J. (1993). Neuron 11, 123–132. Kleene, S. J., Gesteland, R. C., and Bryant, S. H. (1994). J. Exp. Biol. 195, 307–328. Korschen, H. G., et al. (1995). Neuron 15, 627–636. Kramer, R. H., and Siegelbaum, S. A. (1992). Neuron 9, 897–906. Kurahashi, T. (1989). J. Physiol. 419, 177–192. Kurahashi, T. (1990). J. Physiol. 430, 355–371. Kurahashi, T., and Kaneko, A. (1993). J. Physiol. 466, 287–302. Kurahashi, T., and Shibuya, T. (1990). Brain Res. 515, 261–268. Kurahashi, T., and Yau, K. W. (1993). Nature 363, 71–74. Lancet, D. (1986). Annu. Rev. Neurosci. 9, 329–355. Liman, E. R., and Buck, L. B. (1994).Neuron 13, 611–621. Liu, D. T., Tibbs, G. R., and Siegelbaum, S. A. (1996). Neuron 16, 983–990. Lowe, G., and Gold, G. H. (1991). J. Physiol. (Lond.) 442, 147–168. Lowe, G., and Gold, G. H. (1993a). J. Physiol. 462, 175–196. Lowe, G., and Gold, G. H. (1993b). Nature 366, 283–286. Lowe, G., Nakamura, T., and Gold, G. H. (1989) Proc. Natl. Acad. Sci. USA 86, 5641–5645. Lynch, J. W., and Barry, P. H. (1989). Biophys. J. 55, 755–768. Margolis, F. L. (1985). Trends Neurosci. 8, 542–546. Miyamoto, T., et al. (1992). J. Membr. Biol. 127, 173–183. Nakamura, T., and Gold, G. H. (1987). Nature 325, 442–444. Nakamura, T., Lee, H.-H., Kobayashi, H., and Satoh, T.-O. (1996) Biophys. J. 70, 813–817. Nolte, D. L., et al. (1994). J. Chem. Ecol. 20, 1505–1516. Okada, Y., Teeter, J. H., and Restrepo, D. (1994). J. Neurophysiol. 71, 595–602. Okano, M., and Takagi, S. (1974). J. Physiol. (Lond.) 242, 353–370. Ottoson, D. (1956). Acta Physiol. Scand. 35, suppl. 122, 1–83. Pace, U., Hanski, E., Salomon, Y., and Lancet, D. (1985). Nature 316, 255–258. Ramirez-Solis, R., Davis, A. C., and Bradley, A. (1993). Meth. Enzymol. 225, 855–878. Ressler, K. J., Sullivan, S. L., and Buck, L. B. (1993). Cell 73, 597–609. Restrepo, D., Boekhoff, I., and Breer, H. (1993). Amer. J. Physiol. 264, 906–911. Restrepo, D., Miyamoto, T., Bryant, B. P., and Teeter, J. H. (1990) Science 249, 1166–1168. Risser, J. M., and Slotnick, B. M. (1987) Physiol. Behav. 40, 545–549. Schaeren-Wiemers, N., and Gerfin-Moser, A. (1993). Histochemistry 100, 431–440. Schild, D., Lischka, F. W., and Restrepo, D. (1995). J. Neurophysiol. 73, 862–866. Sklar, P. B., Anholt, R. R. H., and Snyder, S. H. (1986) J. Biol. Chem. 261, 15538–15543. Stewart, C. L. (1993). Meth. Enzymol. 225, 823–855. Strotmann, J., et al. (1992).Neuroreport 3, 1053–1056. Szabo, P., and Mann, J. R. (1994). Development 120, 1651–1660. Teicher, M. H., and Blass, E. M. (1977). Science 198, 635–636. Thommesen, G., and Doving, K. B. (1977). Acta Physiol. Scand. 99, 270–280. Vassar, R., Ngai, J., and Axel, R. (1993). Cell 74, 309–318. Wang, H.-W., Wysoki, C. J., and Gold, G. H. (1993). Science 260, 998–1000. Wilkinson, D. G., et al. (1987a). Development 99,493–500. Yamaguchi, M., et al. (1981).. Proc. Natl. Acad. Sci. USA 78, 5817–5820. Zhainazarov, A. B., and Ache, B. W. (1995). J. Neurophys. 74, 479–483.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A viable mouse having a genetic mutation, wherein said mutation effects general anosmia in said mouse by disrupting a function of one or more proteins required for cyclic nucleotide mediated signal transduction in olfactory neurons in said mouse, said protein being an olfactory neuron G protein or an olfactory neuron cycic nucleotide-gated ion channel.

2. A viable mouse having a genetic mutation, wherein said genetic mutation effects general anosmia in said mouse by disrupting a function of a protein required for cyclic nucleotide mediated signal transduction in olfactory neurons in said mouse, said protein being an olfactory neuron cyclic nucleotide-gated cation channel.

3. A method for making a mouse according to claim 1, said method comprising the steps of introducing a genetic mutation in a mouse, wherein said mutation effects general anosmia in said mouse by disrupting a function of one or more proteins required for cyclic nucleotide mediated signal transduction in olfactory neurons in said mouse, said protein being an olfactory neuron G protein or an olfactory neuron cyclic nucleotide-gated ion channel.

4. A method according to claim 3, wherein said genetic mutation disrupts a function of a protein required for cyclic nucleotide mediated signal transduction in olfactory neurons in said mouse, said protein being an olfactory cyclic nucleotide-gated cation channel.

5. A method of characterizing the effect of a stimulus on a mouse, said method comprising the steps of:

contacting a mouse according to claim 1 with a stimulus; and, measuring a response of said mouse to said stimulus;

wherein the presence of said response indicates said stimulus evokes a non-olfactory response in said mouse.

6. A method of characterizing the effect of a stimulus on a mouse, said method comprising the steps of:

contacting a mouse according to claim 2 with a stimulus; and, measuring a response of said mouse to said stimulus;

wherein the presence of said response indicates said stimulus evokes a non-olfactory response in said mouse.

7. A viable mouse having a genetic mutation, wherein said genetic mutation effects general anosmia in said mouse by disrupting a finction of a protein required for cyclic nucleotide mediated signal transduction in olfactory neurons in said mouse, said protein being an olfactory neuron G protein.

8. A method according to claim 3, wherein said genetic mutation disrupts a function of a protein required for cyclic nucleotide mediated signal transduction in olfactory neurons in said mouse, said protein being an olfactory neuron G protein.

9. A method of characterizing the effect of a stimulus on a mouse, said method comprising the steps of:

contacting a mouse according to claim 7 with a stimulus; and, measuring a response of said mouse to said stimulus;

wherein the presence of said response indicates said stimulus evokes a non-olfactory response in said mouse.

\* \* \* \* \*